(12) United States Patent
Lin et al.

(10) Patent No.: US 7,714,026 B2
(45) Date of Patent: May 11, 2010

(54) PHARMACEUTICAL COMPOSITION CONTAINING BAKUCHIOL FOR TREATING WOMAN OSTEOPOROSIS

(75) Inventors: Hang-Ching Lin, Taipei (TW);
Hsiou-Yu Ding, Tainan (TW);
Wen-Liang Chang, Taipei (TW);
Chien-Lian Chao, Taoyuan (TW);
Hsin-Wen Huang, Kaohsiung (TW);
Chin-Liang Lin, Taipei (TW)

(73) Assignee: Sinphar Pharmaceutical Co., Ltd., Taipei (TW)

( * ) Notice: Subject to any disclaimer, the term of this patent is extended or adjusted under 35 U.S.C. 154(b) by 1330 days.

(21) Appl. No.: 11/126,234

(22) Filed: May 11, 2005

(65) Prior Publication Data

US 2005/0256209 A1 Nov. 17, 2005

(30) Foreign Application Priority Data

May 14, 2004 (TW) .............................. 93113777 A

(51) Int. Cl.
*A61K 31/05* (2006.01)
(52) U.S. Cl. ...................................... 514/733
(58) Field of Classification Search .................. 514/733
See application file for complete search history.

(56) References Cited

U.S. PATENT DOCUMENTS

2004/0043089 A1* 3/2004 Rabie ......................... 424/779

FOREIGN PATENT DOCUMENTS

JP 07109225 A * 4/1995
WO WO 01/01996 A1 * 1/2001

OTHER PUBLICATIONS

Krenisky et al. Biol. Pharm. Bull., 1999, vol. 22, No. 10, pp. 1137-1140.*
Katsura et al. Antimicrobia agents and Chemotherapy, 2001, vol. 45, pp. 3009-3013.*
Haraguchi et al. Phytotherapy Research, 2002, vol. 16, pp. 539-544.*
Miura et al. Planta Medica, 1996, vol. 62, pp. 150-153.*
Iinuma et al., English translation of previously cited JP-07109225A, published Apr. 25, 1995.*

* cited by examiner

*Primary Examiner*—James D Anderson
(74) *Attorney, Agent, or Firm*—Bacon & Thomas, PLLC

(57) ABSTRACT

The present invention discloses a novel use of bakuchiol or an extract containing bakuchiol in preventing or treating a woman suffering osteoporosis. An embodiment of this novel use is a pharmaceutical composition containing bakuchiol or an extract containing bakuchiol, which can be in the dosage forms of topical use, oral administration, injection or sustained release. The present invention also discloses a novel use of bakuchiol or an extract containing bakuchiol in preventing or treating a woman suffering breast cancer.

6 Claims, 3 Drawing Sheets

PHARMACEUTICAL COMPOSITION CONTAINING BAKUCHIOL FOR TREATING WOMAN OSTEOPOROSIS

FIELD OF THE INVENTION

The present invention relates to a pharmaceutical composition containing bakuchiol as an effective ingredient for the prevention or treatment of a woman suffering post-menopausal osteoporosis or breast cancer. The present invention also relates to an extract containing bakuchiol capable of preventing or treating a woman suffering osteoporosis or breast cancer.

BACKGROUND OF THE INVENTION

Psoraleae fructus is a ripe fruit of *Psoralea corilifolia* and is traditionally used as a tonic in Chinese herbal medicine. Psoraleae fructus contains many chemical ingredients which have been found possessing pharmacological activities as shown in the literature. Beside lipids, the main chemical ingredients contained in psoraleae fructus include psoralen, isopsoralen and bakuchiol. Among the ingredients, bakuchiol with a phenol terpene structure has received a lot of attention in the past. Many articles related to bakuchiol reveal that bakuchiol has the pharmacological activities as follows: anti-mutation, hepatoprotection, antioxidation, weak estrogen like effect, cytotoxic effect, DNA polymerase inhibitor, anti-inflammation, and antihyperglycemic effect.

Among the patent disclosures, Japan patent publication No. 11-71231 discloses that bakuchiol is capable of inhibiting tyrosinase and can be used in making cosmetics having a skin whitening effect. Japan patent publication Nos. 2000-327581 and 2001-233707 disclose the bacteriostatic effects of bakuchiol, and its use as an agent in sterilizing oral cavity, anti-legionella agent, and anti-MRSA agent. Japan patent publication No. 3-20218 discloses the cellular toxicity of bakuchiol and its use as an anti-corn agent. Japan Patent 7-109225 discloses that lipids in psoraleae fructus are effective in strengthening bone strength through bone calcification.

Current data show that the use of estrogen in treating post-menopausal estrogen-deficient osteoporosis will increase the probability of the subject woman in gaining breast cancer. Thus, there is a pressing need in developing a medicine capable of treating postmenopausal estrogen-deficient osteoporosis without increasing the probability of the subject woman in gaining breast cancer. Of cause, a medicine capable of treating breast cancer, as well as postmenopausal estrogen-deficient osteoporosis is also beneficial.

SUMMARY OF THE INVENTION

The main objective of the present invention is to provide a novel use of bakuchiol or an extract containing bakuchiol in the prevention or treatment of osteoporosis. An embodiment of this novel use is a pharmaceutical composition containing bakuchiol or the extract, which can be in the dosage forms of topical use, oral administration, injection or sustained release.

Another objective of the present invention is to provide a bakuchiol compound or an extract containing bakuchiol in the prevention or treatment of breast cancer. An embodiment of such a use is a pharmaceutical composition for the prevention or treatment of breast cancer. A pharmaceutical composition according to the present invention contains bakuchiol or an extract containing bakuchiol in the prevention or treatment of breast cancer, which can be in the dosage forms of topical use, oral administration, injection or sustained release.

An in vitro cell cultivation test according to the present invention indicates that bakuchiol even at a low concentration has the effect of inhibiting the growth of breast cancer cells. This result shows that bakuchiol has a selective inhibition effect on some human breast cancer cells and is suitable to be used as a therapeutic or preventative agent for breast cancer. This finding on the effect of bakuchiol on human breast cancer cells is different from a previous finding by a Korean scholar: Toxicity of bakuchiol on five different human cancer cells (lung (A549), ovary (SK-OV-3), skin (SK-MEL-2), central nervous system (XF498), and large intestine (HCT)), with an average inhibitory concentration ($IC_{50}$) of 10~15 µg/cc (Arch. Pharm. Res. 15, 356-359 (1992)). The average inhibitory concentrations of those five cancer cells being in such a narrow range indicates that cytotoxicity of bakuchiol is not selective to those five cancer cells. Furthermore, that research does not include human breast cancer cells.

Furthermore, the present invention includes animal tests. The ovary of a female rat was removed to simulate osteoporosis caused by estrogen deficiency. The result shows that bakuchiol at a low dose (5 mg/kg) possess a therapeutic effect on osteoporosis by inhibiting the bone resorption. This finding is different from a previous finding by a Japanese scholar: Lipids in *Psoralea corilifolia* only enhance bone calcification and show no enhancement on bone mass (Japan patent publication No. 7-109225 and Planta med. 62, 150-153 (1996)). The best treatment on osteoporosis lies in a situation where a medicine can promote bone formation and/or inhibit bone resorption. The function of bakuchiol is similar to that of estrogen which includes prevention and treatment of bone resorption. This function obviously is superior than the bone calcification function of the lipids.

From another point of view, the use of estrogen in the treatment of postmenopausal osteoporosis increases the risk of breast cancer. Bakuchiol has the effects in preventing or treating osteoporosis, as well as toxic effect to breast cancer cells. Thus, bakuchiol has the potential in being used as a medicine in preventing or treating a woman suffering from breast cancer/osteoporosis.

Prior art shows that an extract of *Psoralea corilifolia* can be separated into lipids and bakuchiol by silica gel column chromatography. Since the chemical properties thereof are different, they can be easily separated by using thin layer chromatography (TLC), Subsequentyl lipids cannot be seen under an UV lamp but can be detected by an iodine vapor; and bakuchiol can be easily detected by an UV lamp. Therefore, as shown in the following Example 1, only one mixed solution is used to purify and separate lipids and/or bakuchiol.

BRIEF DETAILED DESCRIPTION OF THE DRAWINGS

DETAILED DESCRIPTION OF THE INVENTION

Figure 1:
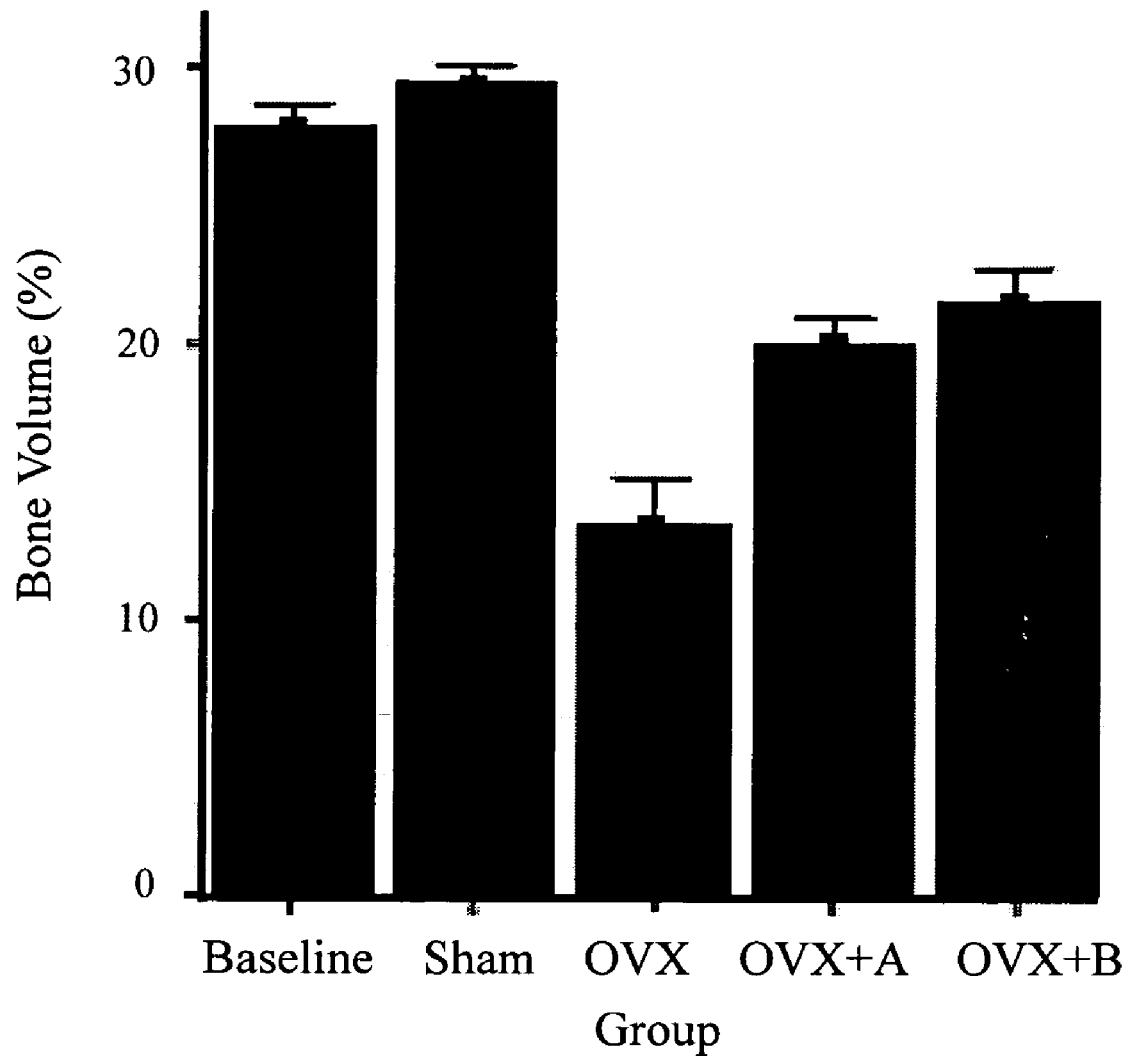
FIG. 1 shows effect of bakuchiol on bone volume of proximal tibia (trabecular bone dominant), wherein Bars show means and error bars show mean+/−1.0 SD.

Preferred embodiments of the present invention includes (but not limited to) the following:

1. A method for treating a woman patient suffering osteoporosis comprising administrating to the patient a therapeutically effective amount of bakuchiol having the following formula (I) or a pharmaceutically acceptable ester or salt thereof in the treatment of woman osteoporosis:

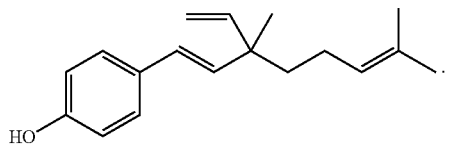

(I)

2. The method as described in Item 1, wherein said bakuchiol or a pharmaceutically acceptable ester or salt thereof is administered through topical application, injection, oral administration, or time release dosage form.

3. The method as described in Item 2, wherein said bakuchiol or a pharmaceutically acceptable ester or salt thereof is administered orally.

4. A pharmaceutical composition for treating woman osteoporosis comprising a therapeutically effective amount in the treatment of woman osteoporosis of bakuchiol having the formula (I) or a pharmaceutically acceptable ester or salt thereof, as an active ingredient, in combination with a pharmaceutically acceptable carrier or diluent used in combination with said effective ingredient, which comprises 5%~95% of bakuchiol (I) by weight of the composition, and is substantially free of psoralen and isopsoralen.

5. The pharmaceutical composition as described in Item 4 comprising 1-300 mg of bakuchiol (I).

6. The pharmaceutical composition as described in Item 4, wherein said pharmaceutical composition is the dosage form of topic use, oral administration, injection or sustained release.

7. The pharmaceutical composition as described in Item 4, wherein said pharmaceutical composition is prepared from *Psoralea corilifolia*.

8. The pharmaceutical composition as described in Item 7, wherein said pharmaceutical composition is prepared according to the following steps:

i) extracting Psoraleae fructus with an organic solvent;
ii) concentrating the resulting solution from the extraction; and
iii) separating the concentrated solution from Step ii) by silica gel chromatography to obtain an extract containing bakuchiol (I) and substantially free of psoralen and isopsoralen.

9. The pharmaceutical composition as described in Item 8, wherein said pharmaceutical composition is in the dosage form of oral administration.

A process for preparing an extract containing bakuchiol according to one of the preferred embodiments of the present invention comprises the following steps:

a) Using an organic solvent, selected from the group consisting of n-hexane, acetone, ethyl acetate, methanol, ethanol, and a mixture thereof, to extract Psoraleae fructus in the form of a powder by grinding;

b) Concentrating the resulting solution from the extraction, separating the concentrated solution with silica gel column chromatography by using a mixed solution of n-hexane and ethyl acetate (n-hexane:ethyl acetate=9:1) as an eluting agent to sequentially obtain an eluate containing (1) lipids and an eluate containing (2) bakuchiol, or collect an eluate containing both the (1) lipids and (2) bakuchiol. After concentrated, the eluate becomes an extract containing bakuchiol, or an extract containing (1) lipids and (2) bakuchiol.

The eluate obtained in step (b) is identified by a thin layer chromatography (TLC), wherein a mixed solution of n-hexane and ethyl acetate (n-hexane:ethyl acetate=9:1) is used as a mobile phase to develop the eluate, and an UV lamp or an iodine vapor is used to identified the lipids and bakuchiol. The chromatography value ($R_f$) for the eluate containing lipids is greater than 0.29 ($R_f$>0.29), while the value for the eluate containing bakuchiol is 0.29 ($R_f$=0.29).

The present invention can be better understood through the following examples, which are illustrative only and not for limiting the scope of the present invention.

Example 1

Three hundred grams of Psoraleae fructus powder was extracted by 2.4 L of acetone, and the mixture was separated into solid and liquid phases. The extraction and solid/liquid separation were repeated three times. The filtrates were combined, and the solvent was removed by evaporation to obtain 72.11 g of an oily extract. Twenty two grams of said oily extract was separated by a silica gel column (9.6×25 cm) packed with 300 g of silica gel (Merck Co., Silica gel 60, mesh 70~230). A mixture of n-hexane/ethyl acetate (9:1), acetone, and methanol were sequentially used as an eluent to elute the column. Twenty five bottles of eluate of n-hexane/ethyl acetate (9:1) were first collected from to elute the column. Furthermore, 10 bottles (Bottle Nos. 26-35) of eluate of acetone were collected from the column, followed by 10 bottles (Bottle Nos. 36-45) of eluate of methanol were collected from the column. Every 300 ml of the eluate was collected separately, i.e. 300 ml per bottle. The eluate was identified by a silica gel thin layer chromatography (TLC) developed by a mixed solution of n-hexane/ethyl acetate (9:1) using an UV lamp or an iodine vapor. The bottles of the eluate containing same ingredients analyzed by TLC were combined.

Eluate in the bottle Nos. 1-7 show no UV absorption spot on the TLC plate, indicating that the eluate contains lipids. The eluate in bottles of No. 1-7 was combined and concentrated to obtain 6.116 g of oily substance. Eluate in the bottles of No. 8-20 show only one UV absorption spot on the TLC plate ($R_f$=0.29). The eluate in the bottles of No. 8-20 was combined and concentrated to obtain 4.543 g of the oily bakuchiol. The eluate in bottles of No. 21-45 containing no bakuchiol was combined and concentrated to obtain 11.04 g of substances. The above mentioned data indicate that: a total of 240.36 g of extract can be obtained per kg of Psoraleae fructus, i.e. an extraction ratio of 24.04%. The 240.36 g of extract contains 66.82 g of lipids (6.68%, based on the weight of Psoraleae fructus), 49.64 g of bakuchiol (4.96%, based on the weight of Psoraleae fructus), and 123.9 g of other Psoraleae fructus ingredients (extraction ratio of 12.4%, based on the weight of Psoraleae fructus).

The structure of bakuchiol was identified with the following data: $[\alpha]_D^{27}$+24° (C 1.0, CHCl3); EI-MS m/z (rel. int. %):

256 ([m]+, 24), 173 (100); UV (EtOH) λ max (log ε): 260 nm (4.26); IR (KBr) υmax 3350, 1650, 1530, 1245, 1010, 980, 922 cm$^{-1}$; $^{13}$C-NMR (δ, CDCl3): C-1 (25.6), C-2 (131.2), C-3 (124.8), C-4 (23.2), C-5 (41.2), C-6 (42.5), C-7 (135.7), C-8 (126.5), C-9 (130.7), C-10 (127.3), C-11 (115.4), C-12 (154.6), C-13 (115.4), C-14 (127.3), C-15 (23.3), C-16 (145.9), C-17 (111.8), C-18 (17.6).

$^{1}$H-NMR (δ mult. (J in Hz), CDCl$_{3}$): H-1 (1.61, S), H-3 (5.15, t (7.3)), H-4 (1.99, q (7.3)), H-5 (1.53, m), H-7 (6.08, d (16.2)), H-8 (6.28, d (16.2)), H-10 (7.26, d (8.5)), H-11 (6.80, d (8.5)), H-13 (6.80, d (8.5)), H-14 (7.26, d (8.5)), H-15 (1.23, S), H-16 (5.91, dd (10.7, 17.4)), H-17 (5.06, m), H-18 (1.71, S)

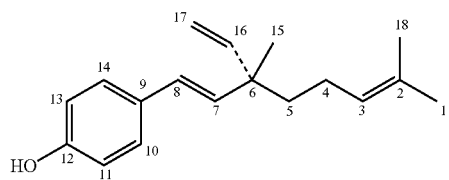

Example 2

Cytotoxicity of Bakuchiol In Vitro

Materials: DMEM (medium), RPMI (medium), L-glutamine, penicillin, streptomycin and FBS (fetal bovine serum) were obtained from Gibco (NY, USA). Culture plasticware was purchased from Corning (MA, USA). Tamoxifen was obtained from Sigma-Aldrich (MO, USA), CCK-8 (Cell counting Kit, a new water soluble tetrazolium salt) was obtained from Dojindo Molecular Technologies (MD, USA). All other chemicals used were of reagent grade and were purchased from Sigma or E. Merck (Germany).

Cell lines and cell cultures: The human breast cancer cell lines T47D and MDA-MB231 were obtained from American Type Culture Collection (ATCC). Of both cancer cells, T47D is estrogen receptor positive, and MDA-MB231 is estrogen receptor negative. Cells were cultured at 37° C. in RPMI medium containing 10% charcoal-dextran stripped fetal bovine serum for T47D cells and in DMEM medium containing 10% charcoal-dextran stripped fetal bovine serum for MDA-MB231 cells with 5% $CO_2$. The cell proliferation was determined by counting the viable cells with trypan blue exclusion.

Cytotoxicity assay: Dispense 198 µl of cell suspension (20,000 cells for T47D per well and 10,000 cell for MDA-MB231 per well) in a 96-well plate and pre-incubate the plate for 24 hours in an incubator at 37° C. with humidified 5% $CO_2$. Then, add 2 µl of various concentrations of tamoxifen, bakuchiol and DMSO (control group) into the culture media in the plate and every concentration was repeatedly added six times. After plate was incubated for 48 hours in the incubator, media were aspirated of and new media (100 µl) were added and incubated for more 1 hour. Add 5 µl of CCK-8 solution to each well of the plate and incubate the plate for 4 hours in the incubator. Measure the absorbance at 450 nm using a ELISA reader. Cytotoxicity of test materials at various concentrations was estimated as the net growth % of cells compared with that of the control group (without test material, net growth=100%). The dose-response curve of test materials were constructed and the $IC_{50}$ value was calculated as the concentration of test material that cause 50% inhibition of cell growth. The result of cytotoxicity of bakuchiol was shown in Table 1.

TABLE 1

In vitro cytotoxicity of bakuchiol to human cancer cell lines

| | Cell lines 50% inhibition of cell growth concentrations of test compounds ($IC_{50}$: µg/cc) | |
|---|---|---|
| Compounds | T47D | MDA-MB231 |
| Tamoxifen | 8.40 | 2.60 |
| Bakuchiol | 5.00 | 0.62 |

As it can be seen from Table 1 that $IC_{50}$ concentrations of bakuchiol are 5.00 and 0.62 µg/cc to human breast cancer cell lines T47D and MDA-MB231, respectively. When human breast cancer cells (T47D/MAD-MB231), with above mentioned $IC_{50}$ concentrations of bakuchiol, were compared with five different human cancer cells, lung (A549), ovary (SK-OV-3), skin (SK-MEL-2), central nervous system (XF498), and large intestine (HCT)), with an average inhibitory concentration ($IC_{50}$) of 10~15 µg/cc of bakuchiol (Arch. Pharm. Res. 15, 356-359 (1992), it indicate that bakuchiol is selective and potent in inhibiting the growth of human breast cancer cell lines. Further, bakuchiol is also superior in inhibiting the growth of human breast cancer cell lines in comparison with Tamoxifen, a drug clinically used for human breast cancer, as shown in Table 1.

Example 3

The purpose of this example is to show the potency of bakuchiol in treating osteoporosis, wherein ovary of a female rat is removed to stimulate osteoporosis caused by estrogen deficiency.

Animal Work

The female Wistar rats of 16 weeks old (unless specified in the other experiment description) were obtained from the stock reared by the Animal breeding center, National Scientific Council in Taipei. These rats were grouped by weights matched in order to distribute the physiological response variation from rats evenly into each group. These rats were grouping as follows:

Baseline group fed with no drug added food (n=8)
Sham operation group fed with no drug added food (Sham) (n=10)
Ovariectomy operation group fed with no drug added food (OVX) (n=8)
Ovariectomy operation group fed with Drug A (5 mg/kg) added food (OVX+A) (n=9)
Ovariectomy operation group fed with Drug B (15 mg/kg) added food (OVX+B) (n=9)

Ovariectomy (removal of ovaries) operation: Ovariectomy was induced using a protocol similar to that described by Wronski et al (Wronski et al, Endocrinology, 123 (2), 681-686 (1998))

During the experiments, the rats were housed in hanging grid cages in groups of two at 21° C. with a 12 hours dark cycle. Food (Rat-mouse diet III, adequate in 1% of calcium content and 1.2% of phosphate content, Purina, USA) was administered by paired feeding between the experimental and control groups. Pair-feeding was carried out by calculating the average amount of food intake in the Sham group. So give the same amount of food to the OVX, OVX+A (5 mg/kg), OVX+B (15 mg/kg) group animals the following day. These animals were fed with a period of two months except for the baseline group which were killed on the very day of doing ovariectomy or sham operation. Rats of OVX+A and OVX+B groups were fed with the usual food chuck but added certain amount of compound A and B in it respectively. Water was given ad libitum to all rats.

Administration of Test Drugs

The test drug was weighted according to dose of 5 mg/kg and 15 mg/kg, and added into the usual food chuck powder and mixed with 10% starch paste. After fully mixed, these chuck powder were made into mass manually and dried by air flow oven. The food with added drug to rats was performed by single blind method.

In Vivo Bone Labelling Procedure and Bone Histomorphometry Assessement

These labeling and bone histomorphometry assessment were done based on standard procedure in bone research (Lin et al, Calcif. Tissue Int., 67, 373-377 (2000)). Specimen were prestained with Villanueva bone stain, then decalcified and embedded in London resin. Undecalcified sections of 7 μm thick were cut using Jung-K microtome (Leica Ltd, USA) and treated with Villanueva stain for observation under light microscopy. Seven μm thick unstained sections were prepared for fluorescent microscopy and assessed with program Osteomeasure (3.0 version, Atlanta, USA). The bone volume (FIG. 1) and eroded surface parameters (FIG. 3) were obtained according to Lin et al. (Lin et al, Calcif. Tissue Int., 67, 373-377 (2000)). The experiment was performed under specific project licences from the Animal Center and IAACU, National Defense Medical Center, National Defense University, Taipei, Taiwan.

Apparent Bone Density Measurement

The whole tibia and femur were stripped off attached muscles and ligaments after sacrifice. An apparent bone density measurement was done based on Archimedes floating principle on an electronic balance set with densitometry frame (Danielsen et al., Calcif. Tissue Int., 52, 26-33 (1993)). The weight of bone measured in the air was marked as W-air. The weight of the same bone weighed in water will be marked as W-water. The apparent bone density was calculated as [W-air/(W-air minus W-water)](gm/cm$^3$) (FIG. 2, Bone apparent density of Tibia).

Data Analysis

These results were expressed as mean and standard deviation (SD) and were transferred to the statistical package of SPSS 8.0 (SPSS Inc, Chicago, USA) for further data processing. The Bonferonni significant difference method was used for postHoc testing the multiple comparisons in one-way ANOVA after it had been showed to be statistical significance.

Figure 2:
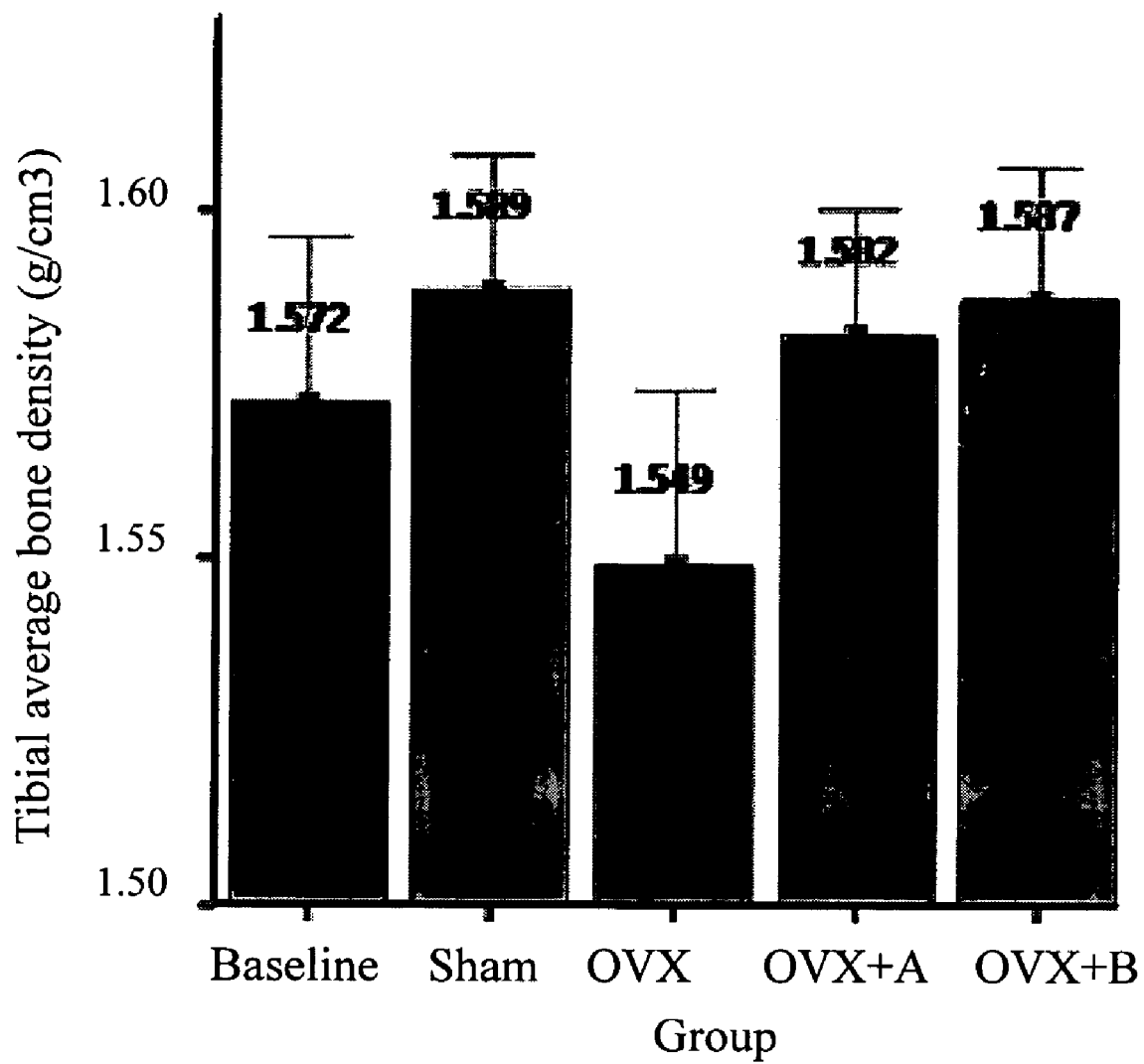
FIG. 2 shows effect of bakuchiol on bone apparent density of tibia, wherein bars shows means and error bars show mean+/−1.0 SD.
Figure 3:
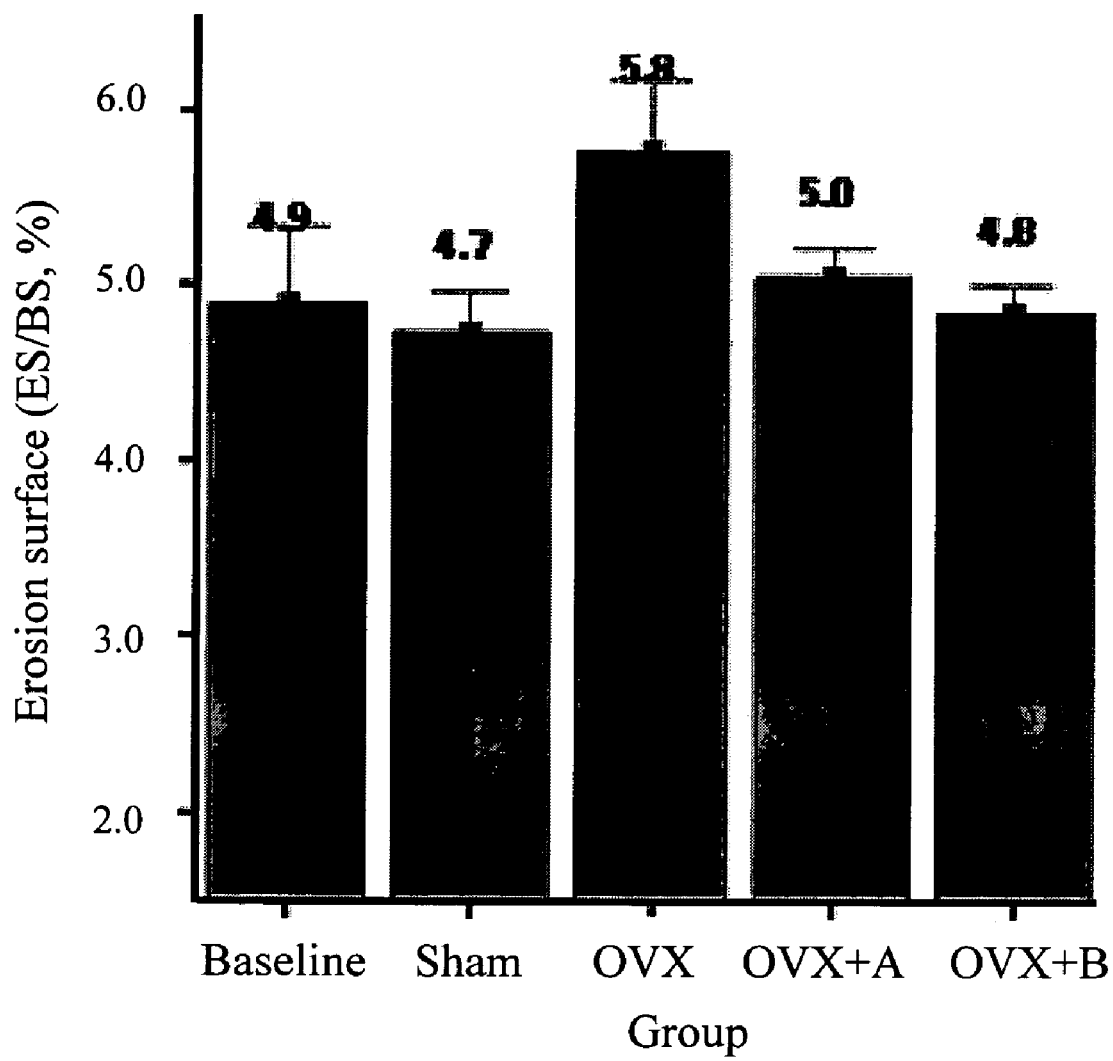
FIG. 3 shows effect of bakuchiol on erosion surface (ES/BS,%) of proximal tibia, wherein bars show means and error bars show mean+/−1.0 SD.

FIGS. 1 and 2 show that the increase in the bone volume and the apparent bone density measured from the OVX+A and OVX+B groups (fed with bakuchiol added) in comparison with the OVX group (fed with no drug added) have statistical significance with $p<0.001$ and $p<0.05$, respectively. Accordingly, bakuchiol is effective in treating osteoporosis caused by post-menopausal estrogen deficiency. The potency mechanism of bakuchiol in treating osteoporosis can be verified by eroded surface parameters. As shown in FIG. 3, rats in the OVX+A and OVX+B groups (fed with bakuchiol added) show the inhibition of bone erosion (bone resorption) by the osteoclast with $p<0.001$ in comparison with the OVX group (fed with no drug added).

The present invention had been described in the above. Any person skilled in the art still could provide various variations and modifications to the present invention without departure from the scope of the present invention, which is defined in the following claims.

The invention claimed is:

1. A method for treating a woman having patient suffering osteoporosis comprising administrating to the patient a composition comprising a therapeutically effective amount of bakuchiol having the following formula (I) or a pharmaceutically acceptable salt thereof for the treatment of a woman osteoporosis wherein said composition is substantially free of psoralen and isopsoralen:

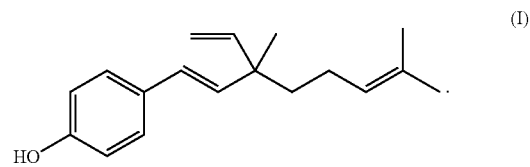

(I)

2. The method as claimed in claim 1, wherein said composition is administered through topical application, injection, oral administration, or time release dosage form.

3. The method as claimed in claim 2, wherein said composition is administered orally.

4. The method as claimed in claim 1, wherein the bakuchiol of formula (I) is isolated from an acetone or ethanol extract from *Psoraleas corilifolia*.

5. The method as claimed in claim 4 wherein the acetone or ethanol extract is concentrated and extracted on a silica gel column with a mixed solution of n-hexane and ethyl acetate.

6. The method as claimed in claim 2 wherein the bakuchiol is isolated from Psoraleae fructus by ethanol or acetone extraction.

* * * * *